United States Patent [19]

Bergink et al.

[11] Patent Number: 5,461,041
[45] Date of Patent: Oct. 24, 1995

[54] PROGESTOGEN-ONLY CONTRACEPTIVE

[75] Inventors: Engelbert W. Bergink, Oss; Herman J. T. C. Bennink, Driebergen, both of Netherlands

[73] Assignee: Akzo Nobel N.V., Velperweg, Netherlands

[21] Appl. No.: 183,644

[22] Filed: Jan. 19, 1994

Related U.S. Application Data

[63] Continuation of Ser. No. 809,722, Dec. 17, 1991, abandoned.

[30] Foreign Application Priority Data

Feb. 17, 1990 [EP] European Pat. Off. ............ 90203371

[51] Int. Cl.$^6$ ..................................................... A61K 31/56
[52] U.S. Cl. .......................... 514/179; 514/182; 514/843
[58] Field of Search ................................... 514/179, 182, 514/843

[56] References Cited

U.S. PATENT DOCUMENTS

| | | | |
|---|---|---|---|
| 4,066,757 | 1/1978 | Pasquale | 524/243 |
| 4,957,119 | 9/1990 | de Nijs | 128/832 |
| 5,088,505 | 2/1992 | de Nijs | 128/830 |
| 5,150,718 | 9/1992 | de Nijs | 128/832 |

OTHER PUBLICATIONS

CA 111(19):168149q, De Nijs, 1989.
S. E. Olsson et al., "Clinical Results with Subcutaneous implant containing 3-keto Desogestrel", pp. 1–11, published Jul., 1990, Contraception 42(1) published in England.
H. Helwig et al., "Helwig Arzneimittel, ein Handbuch fur Arzte und Apotheker", chapter 29–51, 6th Edition, 1988, Germany.
Odlind and Fraser, "Contraception and menstrual bleeding disturbances: A Clinical overview," *Contraception and Mechanisms of endometrail bleeding*, WHO, pp. 5–32, Cambridge University Press, 1990.
Mintz et al., "Contraception with Progestagens in Systemic Lupus Erythematosus," *Contraception*, 30:29–38, 1984.
Tayob et al., "Ultrasound demonstration of increased frequency of functional ovarian cysts in women using progestogen–only oral contraception," British Journal of Obstetrics and Gynaecology, 92:1003–1009, 1985.
Tezabwala et al., "Studies on cell–mediated Immunity in Women Using Different Fertility Regulating Methods," J. Clin. Lab Immunol., 10:199–202 (1983).
E. M. Belsey, "Vaginal Bleeding Patterns Among Women Using One Natural and Eight Hormonal Methods of Contraception," Contraception, 38(2):181–206 (1988).
Bisset et al., "The efficacy of the progestogen–only pill as a contraceptive method," The British Journal of Family Planning, 16:84–87 (1990).
Landgren and Diczfalusy, "Hormonal Effects of the 300ug Norethisterone Minipill," Contraception, 21(1):87–113 (1980).

*Primary Examiner*—Kimberly R. Jordan
*Attorney, Agent, or Firm*—Mary E. Gormley

[57] ABSTRACT

Disclosed is an oral contraceptive regimen containing daily dosage units each containing from 70 to 80 micrograms of desogestrel, 3-ketodesogestrel or mixtures thereof. It has been found that by making a selection of desogestrel or 3-ketodesogestrel at the described dosages in an oral contraceptive regimen administered over the entire menstrual cycle (e.g. 28 days), effective ovulation inhibition is achieved and intermenstrual bleeding is avoided, while acceptable cycle control is retained. Moreover, the regimen also prevents the formation of persistent ovarian cysts.

8 Claims, No Drawings

PROGESTOGEN-ONLY CONTRACEPTIVE

This is a continuation of application Ser. No. 07/809,722 filed Dec. 17, 1991, now abandoned.

TECHNICAL FIELD

The invention relates generally to contraceptive preparations, and more specifically to a contraceptive regimen involving only the administration of desogestrel, 3-ketodesogestrel or mixtures thereof.

BACKGROUND ART

It has been known for some time that contraception can be achieved by the oral administration of sufficient quantities of a progestogen to a female of child-bearing age.

For example in French Patent Application No. 2,223,018 to Ortho Pharmaceutical, a progestogen is administered from at least the fifth day to the twenty-fifth day of the menstrual cycle, the dosage of the progestogen being greater during the last seven days of administration than it is in the first seven days.

U.S. Pat. No. 4,018,919 to Eli Lilly & Co. describes a sequential oral contraceptive method using two different types of progestational agents. These different types of progestational agents are a Type A progestin (e.g. norethindrone) and Type B progestin (e.g. chlormadione acetate).

Another contraceptive regimen using these two types of progestational agents is described in Belgian Patent 773,064 to Ciba Geigy AG.

U.S. Pat. No. 4,171,358 to Eli Lilly & Co. describes another contraceptive method in which a progestin (e.g. chlormadione acetate) is administered on days 6 to 16 of the menstrual cycle, followed by a period in which no hormone is administered.

DT 1,950,857 to Merck Patent GmbH describes a progestogen-only contraceptive pack containing 28 dosage units, 14 to 18 of which are "blanks", containing no contraceptive steroid. Disclosed progestogens include chlormadione acetate, megestrol acetate, melengestrol acetate and medroxyprogesterone acetate. A similar regimen is disclosed in DT 1,965,881, also to Merck Patent GmbH.

U.S. Pat. No. 3,822,355 to Biological Concepts Inc. describes a method of controlling the ovulatory cycle in women involving administering placebo tablets daily for 12 to 16 days; followed administering daily tablets containing 2 to 20 mg progestogen (e.g. norethindrone) for four days; finally followed by administering tablets containing 10 to 40% of the previous progestogen dosage for the remainder of the cycle.

"Progestogen-only pills" are a preferred method of contraception for breast-feeding mothers, older women, Women for whom estrogen is contraindicated, women who are hypertensive, and women who develop migraine headaches when taking a combined pill (i.e. one containing an estrogen and progestogen component). See, e.g. "Contraception for women over the age of 35", *IPPF Medical Bulletin*, 22: 3–4 (1988) and Howie, PW "The progestogen-only pill" *Brit. J. Obstet. Gynaecol.*, 92: 1001–2 (1985).

While different progestogen-only regimens have been described, they are still associated with incomplete ovulation inhibition, and relatively high failure rates. Vessey et al "Progestogen-only oral contraception. Findings in a large prospective study with special reference to effectiveness", *Brit. J. Family Planning*, 292: 526–30 (1986). It has been suggested to increase the daily dosage of progestogen in order to induce complete ovulation inhibition, however such an increase in dosage also increases the frequency of intermenstrual bleeding (i.e. "spotting"), which is clearly not desired. E. Diczfalusy et al, *Progestogens in Therapy*, p. 150 (Raven Press, N.Y. 1983).

Moreover, a high prevalence of functional ovarian cysts have been reported with progestogen only contraceptive regimens, which resolve after discontinuation of the progestogen-only contraceptive. Fotherby, K. "The Progestogen-pill" in: Filshie et al eds. *Contraception: Science and Practice*, pp. 94–108 (1989), and Howie, supra.

A need exists for a progestogen-only contraceptive regimen which more effectively inhibits ovulation, while still not increasing the frequency of intermenstrual bleeding, or leading to persistent functional ovarian cysts.

DISCLOSURE OF THE INVENTION

Surprisingly it has been found that by selecting desogestrel or 3-ketodesogestrel as the progestogen at certain specified dosages for use in an oral contraceptive regimen administered over an entire menstrual cycle (e.g. 28 days), complete ovulation inhibition is achieved, while retaining acceptable cycle control. Moreover, this regimen also seems to prevent the formation of ovarian cysts, and decreases the amount of spotting.

The invention thus includes a drug delivery system containing daily oral dosage units, each unit containing from 70 to 80 micrograms of desogestrel, 3-ketodesogestrel, or mixtures thereof.

The invention also includes a pharmaceutical product (i.e. the dosage units or the package containing the dosage units), a method of using the product, and a process of manufacturing the pharmaceutical product.

The invention also includes a method of providing contraception for a pre-menopausal woman involving orally administering to the woman, on a daily basis, 70 to 80 micrograms of desogestrel, 3-ketodesogestrel, or mixtures thereof.

BEST MODE OF THE INVENTION

Progestogens for use with the invention are 3-ketodesogestrel ("etonogestrel") and desogestrel. Desogestrel has the chemical name 13-ethyl-11-methylene- 18,19-dinor-17α-pregn-4-en-20-yn-17-ol. Desogestrel is believed to be metabolized in the body into 3-ketodesogestrel. In the dosage units, 75 µg of desogestrel or 3-ketodesogestrel are preferably used. Both compounds are available from Organon International, bv of Oss, The Netherlands.

The progestogen ("contraceptive steroid"), is incorporated into dosage units for oral administration. The term "dosage unit" generally refers to physically discrete units suitable as unitary dosages for humans, each containing a predetermined quantity of active material calculated to produce the desired effect.

Methods and compositions for making such dosage units are well-known to those skilled in the art. For example, conventional techniques for making tablets and pills, containing active ingredients, are described in the standard reference, Chase et al., *Remington's Pharmaceutical Sciences*, (16th ed., Mack Publishing Co., Easton. Pa., U.S.A., 1980) (*"Remington's"*), at pages 1553 through 1584. Conventional techniques for making powders, and their composition are described at pages 1535 through 1552 of the reference. Conventional techniques for coating pharmaceutical dosage forms are described at pages 1585 to 1593 of *Remington's*.

For making dosage units, e.g. tablets, the use of conventional additives, e.g. fillers, colorants, polymeric binders and the like is contemplated. In general any pharmaceutically acceptable additive which does not interfere with the function of the active compounds can be used in the one or more of the compositions.

Suitable carriers with which the compositions can be administered include lactose, starch, cellulose derivatives and the like used in suitable amounts. Lactose is a preferred carrier. Mixtures of carriers can also be used.

A process of manufacturing the combination and contraceptive kit of the invention comprises mixing predetermined quantities of desogestrel, 3-ketodesogestrel, or mixtures thereof with predetermined quantities of excipients and converting the mixture into dosage units containing 70 to 80 µg of desogestrel or 3-ketodesogestrel.

Converting the mixture into dosage units generally involves molding the mixture into a tablet, filling a capsule with a dried mixture, or filling a capsule with a wet mixture.

A preferred process of manufacturing the pharmaceutical product according to the invention involves incorporating the desired dosages of contraceptive steroid (i.e. desogestrel, 3-ketodesogestrel, or mixtures thereof) into tablets by techniques such as wet granulation tableting techniques. The package containing the dosage units will contain between 7 and 180, preferably 28, dosage units.

A preferred method of contraception using the invention comprises administering, orally, to a female of child-bearing age, 70 to 80 µg of desogestrel, 3-ketodesogestrel, or mixtures thereof daily. After the completion of one cycle of the regimen, the regimen may be repeated for as long as contraception is desired.

Desogestrel and 3-ketodesogestrel are 70 to 80% bioavailable after oral administration in comparison with non-enteral forms of administration (e.g. via an implant).

The invention is further explained by the following illustrative examples.

EXAMPLE I

The following coated tablets intended for once daily administration were made:

| Compound | Amount (mg/tablet) |
| --- | --- |
| Composition (per tablet): | |
| desogestrel | 0.075 |
| corn starch | 6.500 |
| povidone | 1.950 |
| stearic acid | 0.650 |
| colloidal silicone dioxide | 0.650 |
| dl-α-tocopherol | 0.080 |
| lactose qsad | 65.000 |
| Coating layer: (filmcoat-dry) | |
| hydroxypropylmethylcellulose | 0.75 |
| polyethylene glycol 400 | 0.15 |
| titanium dioxide | 0.1125 |
| talc | 0.1875 |

The tablets were packed in push-through packs. The push through packs are placed in folding cartons, which are additionally sealed in aluminum sachets.

EXAMPLE II

The following tablets intended for once daily administration are made:

| Compound | Amount (mg/tablet) |
| --- | --- |
| 3-ketodesogestrel | 0.075 |
| corn starch | 6.500 |
| povidone | 1.950 |
| stearic acid | 0.650 |
| colloidal silicone dioxide | 0.650 |
| dl-α-tocopherol | 0.080 |
| lactose qsad | 65.000 |
| Coating layer: | |
| hydroxypropylmethylcellulose | 0.75 |
| polyethylene glycol 400 | 0.15 |
| titanium dioxide | 0.1125 |
| talc | 0.1875 |

EXAMPLE III

The tablets of EXAMPLE I, along with similar tablets containing 0.030 and 0.050 mg of desogestrel were tested in 44 healthy female volunteers in a non-public, double-blind randomized study. Ovulation was completely inhibited with the tablets of EXAMPLE I (i.e. those containing 0.075 mg desogestrel), whereas incomplete inhibition of ovulation occurred at the other lower doses. Furthermore, the use of the tablets of EXAMPLE I also had the lowest percentage of bleeding and spotting days (mean of 22%) in comparison to 0.030 mg desogestrel (mean of 32%) and 0.050 mg (mean of 33%). Amenorrhea occurred only once in the group administered the tablets of EXAMPLE I. No luteinized follicles were observed with the group administered the tablets of EXAMPLE I, while the group administered 0.030 mg daily had three cycles, and the group administered 0.050 mg daily had one cycle of luteinized follicles. Non-luteinized small follicular cysts (15–40 mm diameter) were observed in all dose groups during 50 to 75% of the cycles investigated. Persistent cysts occurred in the 0.050 mg group (10 out of 32 cycles). Follicles regressed spontaneously in women administered 0.075 mg desogestrel daily, and persistent cyst formation was not observed in this group.

Reference herein to specific embodiments or examples should not be interpreted as limitations to the scope of the invention, which is defined by the appended claims.

What is claimed is:

1. A pharmaceutical product comprising sequential daily dosage units for oral administration each containing as the sole contraceptively effective ingredient from 70 to 80 µg of a progestogen selected from desogestrel, 3-ketodesogestrel, or mixtures thereof.

2. The pharmaceutical product of claim 1 wherein said pharmaceutical product contains 21 to 35 of said daily sequential dosage units.

3. The pharmaceutical product of claim 2 wherein said progestogen is 3-ketodesogestrel present in a quantity of 75 micrograms per dosage unit.

4. The pharmaceutical product of claim 2 wherein said progestogen is desogestrel present in a quantity of 75 micrograms per dosage unit.

5. A method of providing contraception for a pre-menopausal woman consisting essentially of:

orally administering to a pre-menopausal woman, on a daily basis for as long as contraception is desired, from 70 to 80 micrograms of asteroid selected from the group consisting of 3-ketodesogestrel, desogestrel, and mixtures thereof.

6. The method of claim 5, wherein 75 micrograms of 3-ketodesogestrel are administered.

7. A drug delivery system comprising a package containing 26 to 30 daily sequential dosage units consisting essentially of from 70 to 80 micrograms of a compound selected from the group consisting of desogestrel, 3-ketodesogestrel, and mixtures thereof.

8. A contraceptive kit of the type containing progestogen-only daily dosage units, wherein the improvement comprises the presence of from 70 to 80 micrograms of 3-ketodesogestrel, desogestrel, or mixtures thereof as the progestogen in said daily dosage units.

* * * * *